United States Patent Office

Plant Pat. 2,860
Patented Jan. 28, 1969

2,860
ASH TREE

Markie McCabe, Azusa, Calif., assignor to Monrovia Nursery Company, Azusa, Calif., a corporation of California Filed July 27, 1967, Ser. No. 656,603
1 Claim. (Cl. Plt.—51)

Figure 1:
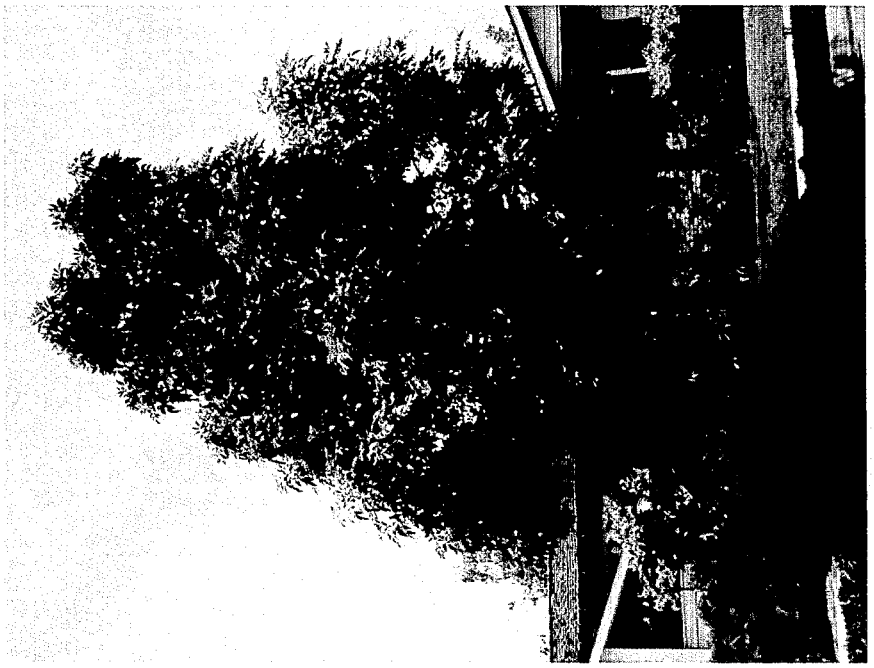

The present invention relates to a new and distinct variety of the Fraxinus genus (ash tree). The newly discovered tree is a new variety of *Fraxinus uhdei,* characterized particularly as to novelty by its large, thick, leathery (coriaceous) dark green compound leaves; by its ability to retain its foliage a longer period of time during winter months (in a mild climate, such as southern California) than previously known *Fraxinus uhdei*; and by its rapid, uniform habit of growth.

The plant was selected from some *Fraxinus uhdei* seedlings being raised by me because of its very large, dark green leaves. No other seedlings have been found in subsequent *Fraxinus uhdei* seedlings raised from seed collected from the same source bearing any similarity to this plant. This plant has never set seed as it is staminate (male). All of the descendants of this plant have been produced by grafting. All have exhibited the same unique characteristics as the original tree, and show that the new variety has become well established.

Figure 2:
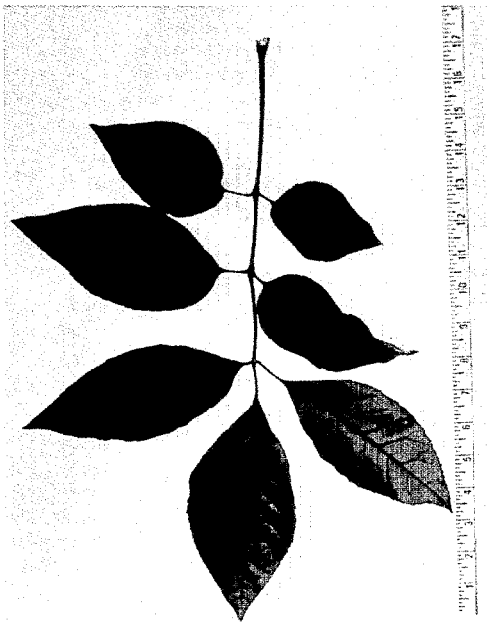
Figure 3:
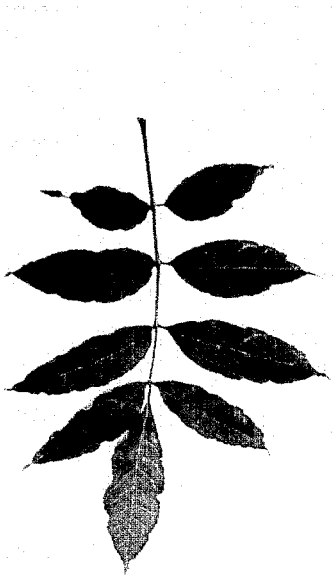

In the drawings (color photographs),

FIGURE 1 is a picture of a fully grown ash tree, showing the characteristic appearance of the new variety; and FIGURES 2 and 3 are comparison pictures of the foliage of the new variety (FIGURE 2) and that of the foliage of the nearest related *Fraxinus uhdei* (FIGURE 3).

A detailed description of the new variety follows and to facilitate identification of the important colors, the color terminology adopted by the British Horticultural Color Charts has been followed:

*The plant*

Parentage: Chance seedling resulting from open pollenation.

*Pollen parent.*—Unknown.

*Seed parent.*—*Fraxinus uhdei.*

Growth: The plant is of vigorous upright growth, branches are ascending and well clothed with foliage. Ultimate height of the plant is estimated to be from 30 to 40 feet, with a spread of from 20 to 25 feet.

Foliage: The leaves are compound, odd pinnate. Usually 7 leaflets, sometimes 5 to 9. Length of leaf from 12 to 16 inches, width from 10 to 12½ inches. The leaves are thick and leathery (coriaceous); the terminal leaflet is broadly elliptic; side leaflets are elliptic to oblanceolate. Edges of leaflets are serrate from apex one-half to two-thirds length of the blade. Edges are slightly revolute, apex acuminate, base attenuate. Rachis and petioles of leaflets are grooved as is leaf petiole.

Color: Dark green (slightly darker than Parsley Green oo962) above. Lighter green (Spinach o960/3) beneath.

Veins: Leaflets are pinnately veined. Midrib is light green above and depressed, midrib below is pale green and prominent. Hairs are found in the axils of the veins and along the sides of the midrib. Hairs extend out on the secondary veins for a short distance.

Arrangement: Leaves are opposite on the branches.

Branches: New growth is a light green in color changing to a gray-green and at maturity silvery-gray with a dark green undertone.

Trunk: Bark on trunk silvery-gray with a faint tinge of red divided by interrupted fissures into broad ridges separating into thin scales on the surface.

I claim:

1. A new and distinct variety of the *Fraxinus uhdei* tree substantially as shown and described, characterized by its upright growing habit, by its unusually large and dark green leathery leaves and by its ability to retain its foliage for a longer period of time during the winter months (of a mild climate) than previously known *Fraxinus uhdei.*

No references cited.

ROBERT E. BAGWILL, *Primary Examiner.*

Jan. 28, 1969 M. McCABE Plant Pat. 2,860

ASH TREE

Filed July 27, 1967

INVENTOR.

MARKIE McCABE,

By Edmond J. Shanahan

ATTORNEY.